United States Patent
Markowitz et al.

(10) Patent No.: US 8,108,043 B2
(45) Date of Patent: *Jan. 31, 2012

(54) METHOD AND SYSTEM FOR DETECTING AND TREATING JUNCTIONAL RHYTHMS

(75) Inventors: H. Toby Markowitz, Roseville, MN (US); Matthew Harris, Cumberland, RI (US); Trina Ann Brand, Derry, NH (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/686,082

(22) Filed: Jan. 12, 2010

(65) Prior Publication Data
US 2010/0179607 A1    Jul. 15, 2010

Related U.S. Application Data

(63) Continuation of application No. 11/565,188, filed on Nov. 30, 2006, now Pat. No. 7,647,105.

(60) Provisional application No. 60/740,947, filed on Nov. 30, 2005.

(51) Int. Cl.
    *A61N 1/362* (2006.01)
(52) U.S. Cl. .......................................................... 607/9
(58) Field of Classification Search .................... 607/9
    See application file for complete search history.

(56) References Cited

U.S. PATENT DOCUMENTS

| | | | |
|---|---|---|---|
| 4,284,082 A * | 8/1981 | Funke et al. | 607/9 |
| 4,920,965 A | 5/1990 | Funke | |
| 5,027,815 A | 7/1991 | Funke | |
| 5,417,714 A * | 5/1995 | Levine et al. | 607/9 |
| 6,493,583 B1 | 12/2002 | Levine | |
| 6,609,028 B2 | 8/2003 | Struble | |
| 6,748,270 B2 | 6/2004 | Rouw | |
| 2001/0031994 A1 * | 10/2001 | Mika et al. | 607/9 |
| 2003/0023281 A1 | 1/2003 | Busch | |
| 2003/0130702 A1 | 7/2003 | Kramer | |

FOREIGN PATENT DOCUMENTS

| | | |
|---|---|---|
| EP | 0451498 | 10/1991 |
| EP | 1449562 | 8/2004 |
| WO | WO 0033914 | 6/2000 |

OTHER PUBLICATIONS

International Search Report, PCT/US2006/061398, Mar. 28, 2007, 8 pages.

* cited by examiner

*Primary Examiner* — Carl H Layno
*Assistant Examiner* — Jeremiah Kimball
(74) *Attorney, Agent, or Firm* — Reed A. Duthler

(57) ABSTRACT

A method and an apparatus for treating cardiac arrhythmias are provided. An interval between first and second consecutive beats of a heart, having first and second chamber types, is determined. The heart is paced at a first rate if the first beat is from the first chamber type and the second beat is from the second chamber type and the interval is less than a predetermined amount of time or if the first and second beats are both from the second chamber type. The heart is paced at a second rate if the first beat is from the first chamber type and the second beat is from the second chamber type and the interval is more than the predetermined amount of time.

20 Claims, 2 Drawing Sheets

METHOD AND SYSTEM FOR DETECTING AND TREATING JUNCTIONAL RHYTHMS

CROSS-REFERENCES TO RELATED APPLICATIONS

This application is a continuation of U.S. patent application Ser. No. 11/565,188, filed Nov. 30, 2006 now U.S. Pat. No. 7,647,105 entitled "METHOD AND SYSTEM FOR DETECTING AND TREATING JUNCTIONAL RHYTHMS", herein incorporated by reference in its entirety.

This application claims the benefit of U.S. Provisional Application No. 60/740,947, filed Nov. 30, 2005, the disclosure of which is incorporated in its entirety.

TECHNICAL FIELD

The present invention generally relates to cardiac pacing therapy methods and systems, and more particularly relates to methods and systems for detecting junctional rhythms and delivering pacing therapies to treat junctional rhythms.

BACKGROUND

In recent years, the use of implantable cardiac devices, such as pacemakers and defibrillators, has become increasingly common. Such devices are now used not only to treat and terminate cardiac arrhythmias, but also to provide valuable information to the clinician regarding the implanted device and its interactions with the patient.

Normal heart rhythm is termed normal sinus rhythm. The initiating impulse for a heart beat normally begins in an area high (towards the patient's head) in the right atrium called the sinus node. Electrical propagation spreads to the left atrium and down the right atrium simultaneously. Mechanical contraction follows electrical activation by a delay in the order of hundreds of milliseconds. At the base of the atria, the electrical signals converge on the atrio-ventricular (AV) node. The AV node conducts electrical impulses slowly from the atria to the ventricles, which provides blood from the atrial contraction time to fill the ventricles. When this relationship is appropriate and normal, as in normal sinus rhythm, the heart is said to be operating with atrio-ventricular (or AV) synchrony.

One type of arrhythmia known as a "junctional rhythm" results in a loss of proper atrio-ventricular synchrony. The term "junction" refers to the "AV junction", also known as the "AV node", and such rhythms are sometimes called nodal rhythms. During a junctional rhythm, the initiating impulse originates in the AV junction. Subsequently, the atria and ventricles are activated electrically and contract mechanically at nearly the same time, since retrograde conduction of the impulse from the AV node to the atria and antegrade conduction from the AV node to the ventricles takes about the same time. Near simultaneous contraction of the atria and ventricles does not allow transport of blood from the atria to the ventricles. The impact of this improper timing includes higher pressures in the atria, retrograde flow of blood into the veins that feed blood to the heart, and lack of ventricular filling. The latter results in a compromised hemodynamic status.

The AV node beats spontaneously at a rate faster than the sinus node or any other part of the heart in order to establish and maintain a junction rhythm. Generally, the portion of the heart which beats most rapidly establishes and controls the cardiac rhythm. If the heart rate is fast, it is called tachycardia. While tachycardia was initially described as greater than 100 beats per minute, it has come to be used in a more relative sense. A heart rate which is faster than appropriate for a given physiologic condition of a patient is now generally considered tachycardia although the rate may be less than the classical threshold of 100 beats per minute. Thus, a junctional rhythm is sometimes called junctional tachycardia.

The source of the junctional beat may also be referred to as an ectopic beat. A beat which originates from a location other than that which would be normal is said to be "ectopic". As example, an ectopic atrial beat is one which does not originate from the sinus node. Beats which originate from the ventricles are ventricular ectopic beats. Junctional rhythms may also be called junctional ectopic tachycardia and abbreviated JET.

Symptoms associated with junctional rhythms are a result of the loss of AV synchrony resulting from aberrations of the normal conduction sequence of the heart. These symptoms may include shortness of breath, choking sensation, chest pain, fatigue, anxiety, dizziness, and confusion, all of which are generally considered to be signs of decreased cardiac output. In some instances, pulsations may manifest in the neck and abdomen of the patient due to the contraction of the atria on closed AV valves, which forces blood back into the venous system. Hypotension, pallor, cool extremities, diaphoresis, reduced urine output, jugular venous distension, ascites, and hepatojugular reflex can also be associated with junctional tachycardia.

Junctional tachycardia occurs frequently following surgical procedures to correct congenital heart defects (often children) and repair heart valves. These rhythms may occur because the patient's sinus node is slow or their AV node is fast. On an ambulatory basis, some patients experience junctional rhythms. Some are brief, infrequent episodes for which patients are asymptomatic, while others produce symptoms and/or are persistent. Since episodes occur infrequently, it is unlikely that such an episode will occur during examination of patients who have implanted devices such as a pacemaker or defibrillator. Junctional rhythms typically are not recognized during routine ambulatory ECG monitoring of patients with devices, as recognition of this arrhythmia is not reported by such systems. However, ambulatory recording with special monitors that incorporate telemetry from the implanted rhythm management device combined with algorithms designed to detect junctional rhythms has demonstrated that junction beats and junctional rhythms exist with a far higher frequency than previously understood in typical pacemaker or defibrillator (ICD) patient populations.

Dual chamber pacemakers and ICDs typically pace and sense the right atrium and right ventricle. Cardiac resynchronization therapy (CRT) devices pace and sense the right atrium, right ventricle and the left ventricle. One feature of such devices is the maintenance of atrio-ventricular synchrony. CRT devices restore and maintain inter ventricular synchrony, between left and right ventricles. These devices prevent bradycardia by maintaining a suitable atrial rate with atrial pacing and (A-V) ventricular synchrony with ventricular pacing. During AV block, ventricular pacing synchronized to spontaneous atrial beats or atrial pacing maintains proper A-V timing. Junctional rhythms, however, often render pacemakers inhibited.

If junctional rhythms produce atrial beats closely followed by ventricular beats, dual chamber pacemakers may sense the atrial beat but the closely following sensed ventricular beat causes the pacemaker to presume the rhythm is normal sinus rhythm, and no pacing will occur. If junctional rhythms produce atrial beats closely following ventricular beats, the action is essentially the same. Sensed ventricular beats cause the timing of the pacemaker to be reset and resume a new timing cycle for subsequent beats. Sequences of consecutive ventricular beats are generally recognized by pacemakers as premature ventricular contractions (PVCs) and recorded as such for later interrogation by clinicians.

Thus, implanted pacemakers are generally ineffective at treating junctional rhythms and physicians are presented with few if any clues in the patient's record as to the possible occurrence of such rhythms. If patients experience infrequent symptoms, their presentation during follow-up is with few if any clues about the possible occurrence of junctional rhythms as the explanation. For the patient in whom junctional rhythms are recognized, therapeutic options are quite limited. Raising the pacemaker rate allows the atrium to become faster than the junctional rhythm, but this option is nearly always unsatisfactory. While raising the rate of pacing when the patient presents in clinic for follow-up may allow restoration of AV synchrony and control of heart rate with the pacemaker at that time, activities of daily living will frequently cause the junctional rhythm to exceed the programmed rate of the pacemaker and loss of AV synchrony will again recur. Reprogramming the pacemaker to a higher rate that will overcome the junctional rhythm completely for all time is often at a rate which can not be comfortably or safely sustained.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary, or the following detailed description. It should also be understood that FIGS. 1-6 are merely illustrative and may not be drawn to scale.

The following description is of a method and system for detecting and treating junctional rhythms. After a junction rhythm is detected, the atrioventricular (AV) interval of the heart is monitored and the pacing rate is adjusted based on the detected AV interval. If the AV interval falls below a predetermined threshold (e.g., 125 mS), the pacing rate is increased. If the AV interval rises above (or greater than or equal to) the predetermined threshold, the pacing rate is decreased. Even if during pacing, the detected AV interval indicates that the heart is in proper AV synchrony, the pacing rate may still be reduced to test whether or not the heart is still experiencing a junctional rhythm. If the heart is still experiencing a junctional rhythm and the pacing rate is reduced to a rate that is below the junctional rhythm rate, the AV interval will decrease. Once the AV interval decreases below the predetermined threshold, the pacing rate is again increased until proper AV synchrony is achieved. This is repeated periodically to accommodate varying conditions of the patient and the junctional rhythm. Thus, the method and system pace the heart at the lowest possible rate to maintain proper AV synchrony.

Figure 1:
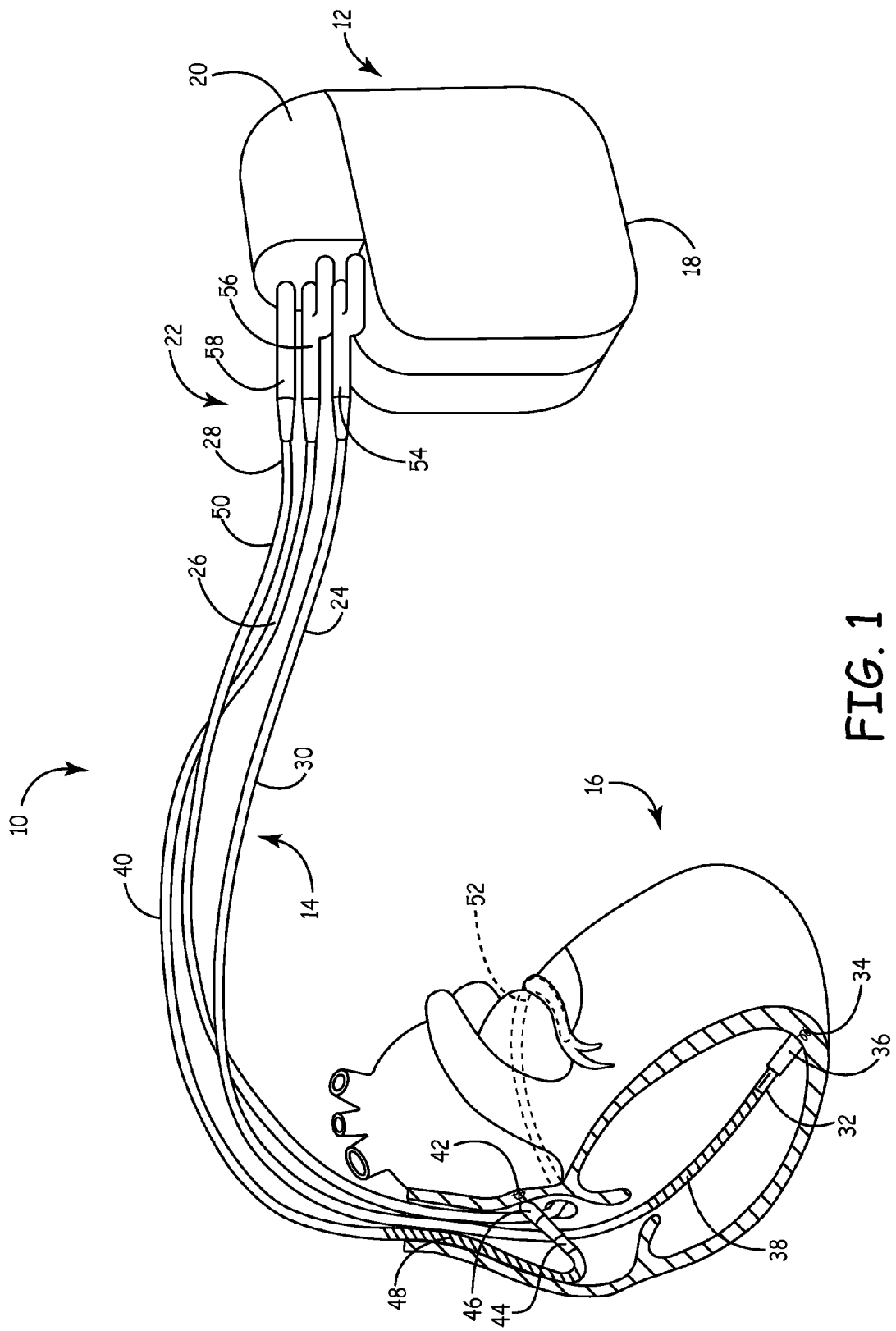
FIG. 1 is an isometric view of a cardiac treatment system, including an implantable cardiac device and a lead set.

FIG. 1 illustrates a cardiac treatment system 10 according to one embodiment of the present invention. The system 10 includes an implantable cardiac device, or implantable cardioverter defibrillator (ICD), 12 and a lead set 14, which are connected to a heart 16. The ICD 12 includes a housing 18, a connector block 20, and lead connector assemblies 22. The ICD 12 may be, for example, a pacemaker, cardioverter, and/or defibrillator, as is commonly understood in the art. Although not illustrated in detail, an uninsulated portion of the housing 18 may function as an electrode to defibrillate either the atria or ventricles of the heart. This uninsulated portion may also be used as an electrode for sensing, pacing and other electrical measurements such as by measuring impedance for a variety of diagnostic functions.

The lead set 14 includes a ventricular lead 24, an atrial/superior vena cava (SVC) lead 26, and a coronary sinus lead 28. As will be appreciated by one skilled in the art, the ICD 12 and the lead set 14 illustrated in FIG. 1 are in the form of a "transvenous" ICD system, as the leads 24, 26, and 28 have been inserted into the heart 16 through the venous system. The ventricular lead 24 includes an elongated insulated lead body 30 that carries three concentric coiled conductors, separated from one another by tubular insulated sheaths. The ventricular lead 24 also includes a ring electrode 32, an elongated coil electrode 38, and an extendable helix electrode 34, mounted retractably within an insulated body 36. Although not specifically illustrated, electrodes 32, 34 and 38 are each coupled to one of the coiled conductors within lead body 30 and can be used for both ventricular pacing and sensing of ventricular depolarizations.

The atrial/SVC lead 26 includes an elongated insulated lead body 40, similar to lead body 30, carrying three concentric coiled conductors, separated from one another by tubular insulated sheaths. The atrial/SVC lead 26 also includes a ring electrode 44 and an extendable helix electrode 42, mounted retractably within an insulated body 46. The distal end of lead body 40 is preformed to retain a J-shape at the distal end. The electrodes 42 and 44 are each coupled to one of the coiled conductors within lead body 40 and are employed for atrial pacing and sensing of atrial depolarizations. An elongated coil electrode 48 is provided proximal to ring electrode 32 and coupled to the third conductor within lead body 40.

Lead 28, lead body 50, and hidden lead body profile 52 at the distal end thereof are placed through the coronary sinus, venous drainage from the heart's circulation, and into a further tributary such as the great cardiac vein. The distal end of lead body 50 includes an electrode, not shown in FIG. 1, for use in pacing and sensing the left ventricle.

The lead connector assemblies 22 include a right ventricular lead connector 54, an atrial/SVC lead connector 56, and a left ventricular lead connector 58. The right ventricular lead connector 54 is bifurcated and carries two electrical connectors. The atrial/SVC lead connector 56 is bifurcated but carries three electrical connectors, each coupled to a respective conductor within the ventricular lead connector 54. The lead connector 58 is connected to the single conductor within the lead body 50. The leads 24, 26, and 28 through the lead connectors 54, 56 and, 58 pass into the connector block 20. Electrical and mechanical connections are made in connector block 20 such that each conductor is electrically routed into the housing 18.

Figure 2:
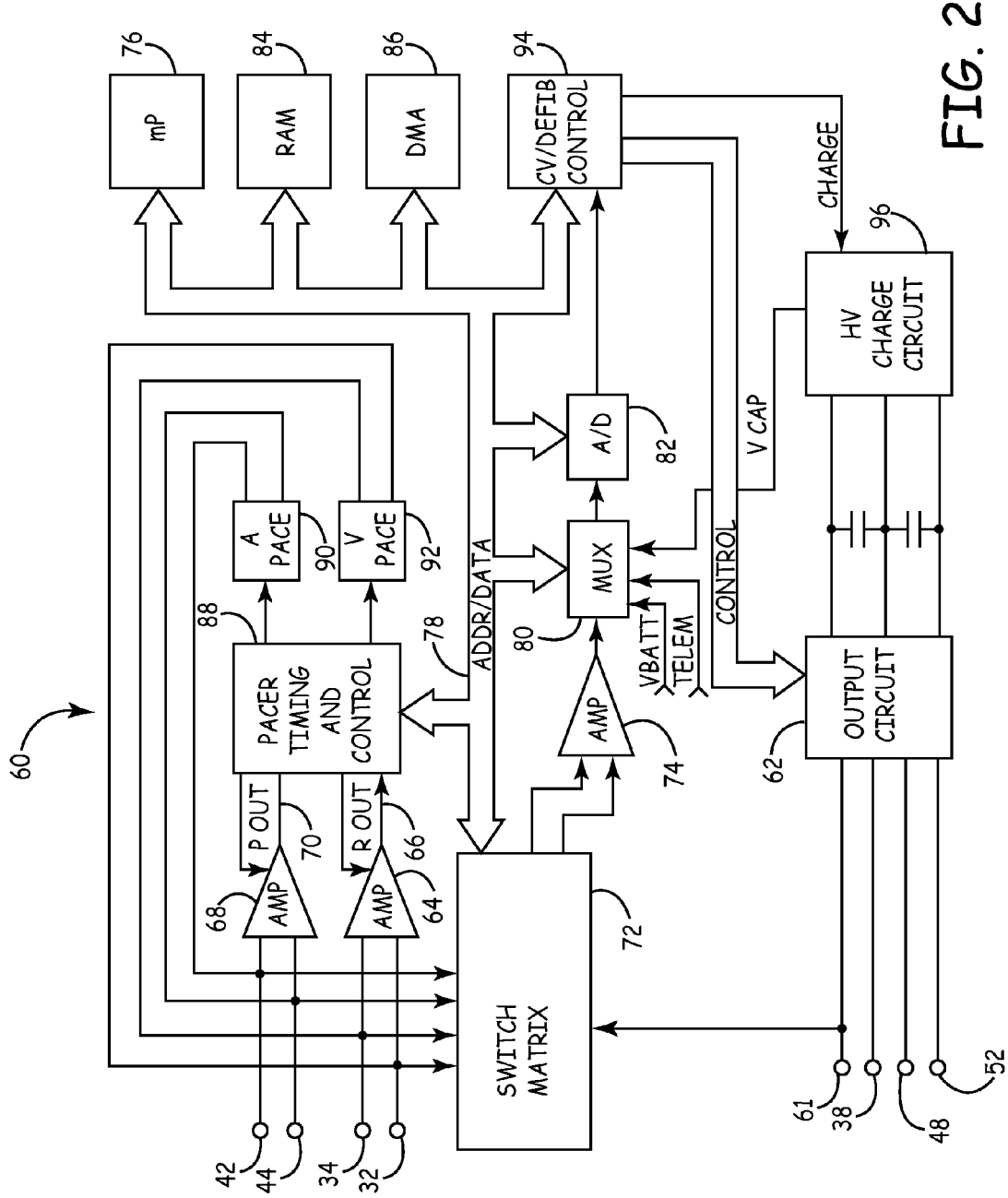
FIG. 2 is a block diagram of a system within the implantable cardiac device illustrated in FIG. 1.

FIG. 2 is a functional block diagram illustrating a system capable of performing the methods of detecting and treating cardiac arrhythmias, according to one embodiment of the present invention. The system 60 may be implemented within the ICD 12 of FIG. 1 and may take the form of an implantable device that integrates various pacemaker/cardioverter/defibrillator functions. FIGS. 1 and 2 are exemplary of the type of device in which the invention may be embodied, as the invention may be practiced in a wide variety of device implementations, including devices providing therapies for treating atrial arrhythmias, ventricular arrhythmias, and junctional rhythms. In addition, the invention may be practiced in pacemakers that do not provide cardioversion or defibrillation, as well as devices that deliver different antiarrhythmic therapies such as nerve stimulation or drug administration. As will be appreciated by one skilled in the art, the system 60 illustrated in FIG. 2 may be appropriate for pacing and sensing two chambers of a heart. A system suitable for pacing and sensing three chambers of the heart, such as in cardiac resynchronization therapy (CRT), would include, in addition to the components described below, an additional sense amplifier, blanking control and signals for the third sense amplifier, and an LV pacing output circuit.

In the example illustrated in FIG. 2, electrodes 32, 34, 38, 42, 44, and 48 represent the electrodes designated by similar reference numerals shown in FIG. 1, as well as the electrode on the distal end of the lead body 50. Likewise, electrode 61 represents the uninsulated portion of the housing 18 of device 10, as illustrated in FIG. 1, which may function as a defibrillation, sensing, pacing, and measurement electrode. Referring again to FIG. 2, electrodes 61, 38, and 48 are coupled to a high voltage output circuit 62 (e.g., pulse generator). Electrodes 32 and 34 are coupled to an R-wave amplifier 64 for the right ventricle, which preferably takes the form of an automatic gain controlled amplifier providing an adjustable sensing threshold as a function of the measured R-wave signal. A signal is generated on an R-out line 66 whenever the signal sensed between electrodes 32 and 34 exceeds the present sensing threshold.

Electrodes 42 and 44 are coupled to a P-wave amplifier 68, which also may take the form of an automatic gain controlled amplifier providing an adjustable sensing threshold as a function of the measured P-wave amplitude. A signal is generated on a P-out line 70 when the signal sensed between electrodes 42 and 44 exceeds the sensing threshold. A switch matrix 72 selects which of the available electrodes are coupled to a wide band amplifier 74 for use in digital signal analysis. The selection of which of the electrodes are to be operated is controlled by a controller, which may take the form of a microprocessor (μP) 76. The μP 76 controls selection of the electrodes via the switch matrix 72 through a data/address bus 78. Signals from the electrodes selected for coupling to the wide band amplifier 74 are provided to a multiplexer (MUX) 80 and thereafter converted to multi-bit digital signals by an analog-to-digital (A/D) converter 82, for storage in a random access memory (RAM) 84 under control of a direct memory access (DMA) circuit 86.

The μP 76 may preferably employ digital signal analysis techniques to characterize the digitized signals stored in the RAM 84 to recognize and classify the heart rhythm (e.g., normal sinus rhythm, arrhythmia, etc.) using any of a variety of known signal processing methods. In particular, the μP 76 may implement a detector that monitors the cycle length and regularity of the heart rhythm to identify and classify an arrhythmia. The remainder of the circuitry illustrated in FIG. 2, such as pacer timing and control circuitry 88, output circuits (i.e., A pace circuit 90 and V pace circuit 92), cardioversion/defibrillation control circuitry (CV/DEFIB Control) 94, and high voltage charging circuit 96, is dedicated to the provision of cardiac pacing, cardioversion, and defibrillation therapies. The μP 76 is programmed to control the circuitry of FIG. 2 to detect and classify different heart rhythms, make and record measurements, and deliver pacing therapies.

Although not specifically illustrated, it should be understood that the system 60, either as hardware or instructions stored, for example, within the μP 76, the RAM 84, and/or pacer timing and control circuitry 88, also includes various predetermined AV intervals, such as lower and upper AV interval rate limits, rate-adaptive AV intervals, and separate AV intervals associated with atrial pacing and atrial sensing. These AV intervals are adjustable by, and information stored in the ICD 12 is accessible to, a user (e.g., physician, nurse, or technician) of the system 60 illustrated in FIG. 1 through a telemetry system. Also included are various V-V intervals, or interventricular intervals (i.e., the time intervals between successive, but not necessarily consecutive, premature ventricular beats), such as the time between sensing on a right ventricular lead and pacing on the left ventricular lead, sensing on a left ventricular lead and pacing on the right ventricular lead, pacing on the left ventricular lead followed by pacing on the right ventricular lead, and/or pacing on the right ventricular lead followed by pacing on the left ventricular lead. The system 60 also includes (e.g., stored on RAM 84) instructions for carrying out the methods and processes described below.

In use, referring again to FIG. 1, after the treatment system 10 has been surgically implanted into the patient, the system 60 may apply anti-bradycardia pacing, anti-tachyarrhythmia pacing or other pacing therapies to the heart 16, or may simply monitor the activity of the heart 16 (i.e., detection mode).

A method for detecting and treating a junctional rhythm uses the ICD 12 described above.

The ICD 12 "suspects," or makes a preliminary detection of, a junctional rhythm in the heart of the patient. The ICD 12 may make the preliminary detection of the junctional rhythm through the electrodes by, for example, either detecting an atrial depolarization just before a ventricular depolarization or detecting ventricular depolarizations in the absence of atrial depolarizations. That is, the ICD 12 suspects a junctional rhythm if two consecutive beats of detected, one being an atrial beat and the other being a ventricular beat, and the interval between the two beats is less than the predetermined threshold described above. The ICD 12 also suspects a junctional rhythm if the two consecutive beats are both ventricular beats, with no atrial beat occurring in the interval between.

After the ICD 12 has made the preliminary detection of the junctional rhythm, the ICD 12 may then attempt to control the ventricular rate using atrial pacing. The ICD first determines the RR interval (i.e., time between ventricular beats). Then, it is determined whether or not the RR interval (i.e., the ventricular rate) is stable. The ventricular rate may be deemed to be stable if the RR interval stays within a predetermined threshold, which may be based on the first several RR intervals that are detected. If the ventricular rate is not stable, no attempt is made to treat the arrhythmia.

If it is determined that the RR interval is stable, an atrial pace is scheduled and inserted at an appropriate interval before the next ventricular beat. In one embodiment, the atrial pace is inserted between 100 and 200 ms before the next anticipated ventricular beat. The inserted atrial pace may be the beginning of an atrial pacing session or a rescheduled atrial pace of a pacing therapy that had already started. Following the atrial pace, it is again determined whether or not the ventricular rate is stable (i.e., the atrial paces are followed by a constant ventricular beat). If the ventricular rate is not stable, no attempt is made it treat the arrhythmia.

If the ventricular rate remains stable after atrial pacing has begun, the atrial pacing rate is changed (from a first test rate to a second test rate), and the ventricular rate is again checked to see if the RR interval has changed according to the new atrial pacing rate. In one embodiment, the atrial pacing rate is increased by approximately 5 bpm. If the R-wave follows the atrial stimulus provided by the atrial pacing, the ventricular rate will also increase similarly to the atrial pacing rate. If the ventricular rate follows the change in atrial pacing, it is assumed that the heart is not experiencing a junctional rhythm. However, if the ventricular rate does not follow the change in atrial pacing, a junctional rhythm treatment therapy is delivered, as will be described below.

With the determination having been made that the heart is experiencing a junctional rhythm, the ICD 12 determines the interval between two consecutive beats of the heart. As described before, one of the beats may be an atrial beat and the other may be a ventricular beat, or both beats may be ventricular beats.

A determination is made as to whether or not both beats are ventricular beats. If both beats are ventricular, the atrial pacing rate is increased from an initial rate or initiated if pacing had not yet commenced. The interval between the next two consecutive beats is determined.

If one of the beats is an atrial beat and the other is a ventricular beat, it is determined whether or not the AV interval (i.e., the time between the atrial beat and the ventricular beat) is within the normal AV interval limits that are stored in the memory of the ICD. In one embodiment, the AV interval limits range between 100 and 150 ms. That is, if the AV interval is between 100 and 150 ms, the heart is determined to be in normal AV synchrony. In another embodiment, the AV interval limits cover only a single AV interval (i.e., a target AV interval, such as 120 ms). In such an embodiment, if the sensed AV interval is not exactly 120 ms, the AV interval is determined not to be within the AV interval limits.

If the AV interval is not within the AV interval limits, it is determined whether or not the sensed AV interval is greater than the AV interval limits. If the AV interval is greater than the AV interval limits, or the target AV interval, the atrial pacing rate is decreased. If the sensed AV interval is not greater than the AV interval limits, it is determined whether or not the AV interval is less than the AV interval limits. If the sensed AV interval is less than the AV interval limits, the atrial pacing rate is increased.

Thus, the atrial pacing rate is essentially slowed to provide a measure of AV conduction time. Once the atrial pacing rate has slowed below the rate of the junctional rhythm, the time between the atrial stimulus (or beat) and the detection of the ventricular beat will decease. If the atrial pacing rate becomes too slow, the junctional rhythm will dominate and the ventricular beat from the junctional rhythm may precede the atrial pace, at which point the atrial pacing rate is increased. In this way, a search is continuously made for the proper atrial pacing rate to provide proper AV synchrony.

The rate at which the atrial pacing is increased may differ depending on whether the two consecutive beats are both ventricular or the sensed AV interval is less than the AV interval limits. In one embodiment, the atrial pacing rate is increased by 1 bpm per beat if the sensed AV interval is less than the AV interval limits. The atrial pacing rate may be increased more quickly (e.g., 2 bpm per beat) if both beats are determined to be ventricular beats.

Referring again to FIG. 2, during operation, various types of data may be stored by the system 60 (e.g., in the microprocessor 76, RAM 84, DMA 86, or other memory). The system 60 records and stores information relative to heart rhythms and interaction of the ICD 12 with the heart 16. For example, specific information is maintained regarding each beat and whether it was paced or sensed in the atrium and, similarly, paced or sensed in the ventricle. The system 60 also recognizes and stores time-stamped episodes along with their duration, the rate at which they occurred, and the activity level of the patient (i.e. sensor derived rate for rate response). Such information will enable a clinician to recognize occurrences of junctional rhythms in the patient and appropriately adjust any settings within the ICD 12, as well as prescribe other treatments to prevent future occurrences. As will be appreciated by one skilled in the art, the information stored within the system 60 may be accessed by the clinician through a telemetry system.

One advantage of the method and apparatus described above is that junctional rhythms may be detected and treated by an ICD. Another advantage is that during an occurrence of a junction rhythm, proper AV synchrony is restored to the heart while pacing the heart at the slowest rate possible. A further advantage is that because the slowest possible pacing rate which will retain proper AV synchrony is constantly be sought, if the heart becomes capable to operate with a normal sinus rhythm, the pacing rate will drop below the sinus rate and the pacing will cease.

Other embodiments may utilize other types of ICDs besides transvenous, such as epicardial and subcutaneous ICDs. The methods and algorithms described above may be implemented separately, or in combination as a single method to detect and treat junctional rhythms.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method for treating junctional rhythms comprising: determining an interval between first and second consecutive beats of a heart having first and second chamber types; pacing the heart at a first rate when the first beat is from the first chamber type and the second beat is from the second chamber type and the interval is less than a predetermined amount of time; pacing the heart at said first rate when the first and second beats are both from the second chamber type; and pacing the heart at a second rate when the first beat is from the first chamber type and the second beat is from the second chamber type and the interval is more than the predetermined amount of time.

2. The method of claim 1, wherein the first pacing rate is greater than the second pacing rate.

3. The method of claim 2, wherein the predetermined amount of time is a range between a lower interval limit and an upper interval limit.

4. The method of claim 3, further comprising pacing the heart at an initial pacing rate and wherein said pacing at the first rate comprises increasing the initial pacing rate at a first pacing increase rate if the first beat is from the first chamber type and the second beat is from the second chamber type and the interval is less than the lower interval limit and increasing the initial pacing rate at a second pacing increase rate if the first and second beats are both from the second chamber type, the second pacing increase rate being greater than the first pacing increase rate.

5. The method of claim 4, wherein the first chamber type is an atrium and the second chamber type is a ventricle.

6. The method of claim 5, wherein said pacing and said determining are performed with an implantable cardioverter defibrillator (ICD) implanted subcutaneously in a patient.

7. The method of claim 6, further comprising repeating said pacing and said determining for a plurality of sets of consecutive beats.

8. The method of claim 7, wherein the lower interval limit is approximately 100 ms and the upper interval limit is approximately 150 ms.

9. The method of claim 8, wherein said pacing is atrial pacing and further comprising determining a ventricular rate of the heart and pacing the heart at a test pacing rate, said pacing at the test pacing rate comprising inserting an atrial pace a predetermined AV interval before a next ventricular beat.

10. The method of claim 9, further comprising:
changing the test pacing rate; and
determining the ventricular rate after said change in the test pacing rate.

11. An implantable cardiac device comprising: a housing; a sense amplifier within the housing and responsive to depolarizations of at least one chamber type of a heart, the heart having first and second chamber types; a pulse generator within the housing to produce cardiac stimulation pulses to the heart; and a controller within the housing and coupled to the sense amplifier and the pulse generator, the controller configured to deliver a junctional rhythm therapy comprising: determining an interval between first and second consecutive beats of a heart having first and second chamber types;
pacing the heart at a first rate when the first beat is from the first chamber type and the second beat is from the second chamber type and the interval is less than a predetermined amount of time; pacing the heart at said first rate when the first and second beats are both from the second chamber type; and pacing the heart at a second rate when the first beat is from the first chamber type and the second beat is from the second chamber type and the interval is more than the predetermined amount of time.

12. The device of claim 11, wherein the first pacing rate is greater than the second pacing rate and the predetermined amount of time is a range between a lower interval limit and an upper interval limit.

13. The device of claim 12, wherein the controller is further configured to pace the heart at an initial pacing rate and wherein said pacing at the first rate comprises increasing the initial pacing rate at a first pacing increase rate if the first beat is from the first chamber type and the second beat is from the second chamber type and the interval is less than the lower interval limit and increasing the initial pacing rate at a second pacing increase rate if the first and second beats are both from the second chamber type, the second pacing increase rate being greater than the first pacing increase rate.

14. The device of claim 13, wherein the first chamber type is an atrium and the second chamber type is a ventricle.

15. The device of claim 14, further comprising a memory within the housing to record the intervals between the first and second consecutive beats and the occurrences of the first and second pacing rates.

16. A method for treating cardiac arrhythmias comprising: determining an interval between first and second consecutive beats of a heart having an atrium and a ventricle; when the first beat is an atrial beat and the second beat is a ventricular beat and the interval is less than a predetermined amount of time, determining a ventricular rate for the heart; when the first and second beats are both ventricular beats, determining a ventricular rate for the heart; pacing the heart at a first test pacing rate, said pacing at the first test pacing rate comprising inserting an atrial pace a predetermined AV interval before a next ventricular beat; pacing the heart at a second test pacing rate; re-determining the ventricular rate of the heart after said pacing at the second test pacing rate; and delivering a junctional rhythm therapy to the heart if the ventricular rate does not match the second test pacing rate.

17. The method of claim 16, further comprising aborting said delivery of the junction rhythm therapy if the ventricular rate is not stable.

18. The method of claim 17, wherein said delivery of the junction rhythm therapy comprises:
if the first beat is an atrial beat and the second beat is a ventricular beat and the interval is less than a predetermined amount of time or if the first and second beats are both ventricular beats, pacing the heart at a first rate; and
if the first beat is an atrial beat and the second beat is a ventricular beat and the interval is more than the predetermined amount of time, pacing the heart at a second rate.

19. The method of claim 18, wherein the first pacing rate is greater than the second pacing rate and said pacing at the first rate comprises increasing the initial pacing rate at a first pacing increase rate if the first beat is from the first chamber type and the second beat is from the second chamber type and the interval is less than a lower interval limit and increasing the initial pacing rate at a second pacing increase rate if the first and second beats are both from the second chamber type, the second pacing increase rate being greater than the first pacing increase rate.

20. The method of claim 19, wherein the predetermined amount of time is a range between approximately 100 ms and 150 ms.

* * * * *